US00PP13821P29

(12) United States Plant Patent

Yamaguchi

(10) Patent No.: US PP13,821 P2

(45) Date of Patent: May 20, 2003

(54) *CORYLOPSIS SPICATA* PLANT NAMED 'GOLDEN SPRING'

(75) Inventor: Seiju Yamaguchi, Gifu Prefecture (JP)

(73) Assignee: Hines Nurseries, Inc., Irvine, CA (US)

( * ) Notice: Subject to any disclaimer, the term of this patent is extended or adjusted under 35 U.S.C. 154(b) by 0 days.

(21) Appl. No.: 09/544,008

(22) Filed: Apr. 6, 2000

(51) Int. Cl.[7] ..... A01H 5/00

(52) U.S. Cl. ..... Plt./216

(58) Field of Search ..... Plt./216

*Primary Examiner*—Bruce R. Campell
*Assistant Examiner*—Michelle Kizilkaya
(74) *Attorney, Agent, or Firm*—Christie, Parker & Hale, LLP

(57) ABSTRACT

A new plant variety of *Corylopsis spicata* characterized by having distinctively yellow colored foliage during the growing season.

1 Drawing Sheet

BACKGROUND OF THE INVENTION

Figure 1:
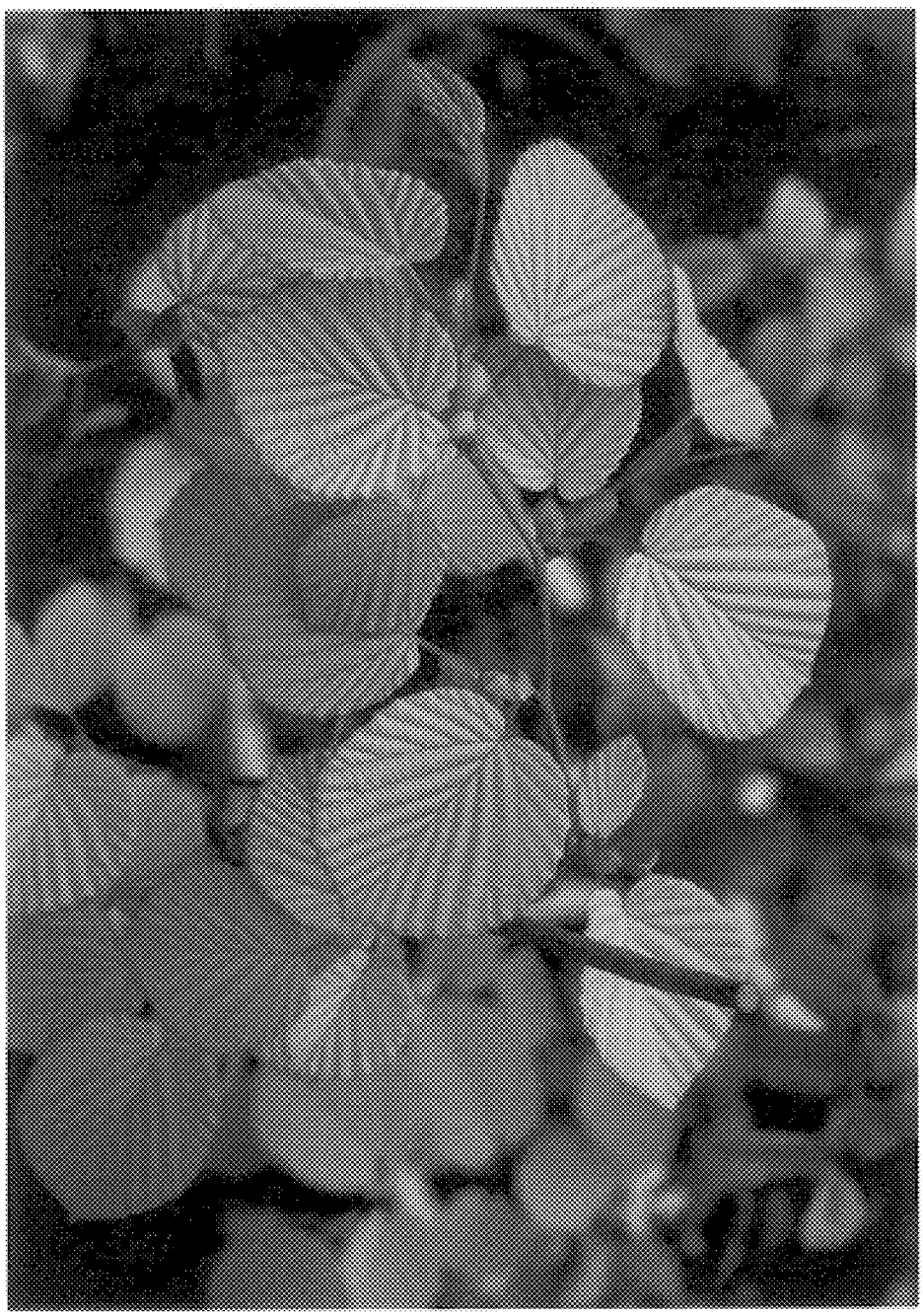

The present invention relates to a new and distinct variety of *Corylopsis spicata* Sieb. & Zucc. which was discovered as a chance seedling (natural mutation) in a controlled planting of *Corylopsis spicata* (unnamed, unpatented) by Mr. Seiju Yamaguchi, in Gifu Prefecture, Japan. The varietal denomination of the new variety is 'GOLDEN SPRING'.

The genus Corylopsis is included in the family Hamamelidaceae which comprises about 28 genera and 90 species of deciduous or evergreen trees and shrubs growing in the northern and southern hemispheres. The genus is currently in taxonomic flux with the reported number of species ranging from 12 to 30, inhabiting the region from Bhutan to Japan; all species are deciduous. They are generally spreading shrubs or, rarely, small trees with the primary ornamental feature being early spring blooms.

*Corylopsis spicata* is native to Japan and has alternate, simple leaves, 4 to 11 cm long, 4 to 9 cm wide, orbicular-ovate or orbicular-obovate, acuminate to abruptly short acuminate, base rounded to cordate to obliquely cordate, glabrous above, glaucous and pubescent beneath, sinuate-denticulate with bristle-like teeth, palmately veined with 6 to 7 pronounced vein pairs, petiole 1 to 2.5 cm long and densely pubescent. The new growth is purplish, alter becoming dull dark to blue green.

Flowers of *Corylopsis spicata* are fragrant, bright yellow and borne in 6 to 12 flowered, 2 to 6 cm long pendulous pubescent racemes in early to mid spring.

SUMMARY OF THE INVENTION

The new variety was discovered as a chance seedling (natural mutation) in a controlled planting and differs from its parent in having striking yellow foliage. Asexual reproduction of the new variety by grafting in Gifu Prefecture, Japan and Lewisberry, Pa. has confirmed that the distinctive characteristics of the new variety are stable and transmitted to succeeding generations, and the new variety reproduces true to type.

COMPARISON WITH PARENT

'GOLDEN SPRING' is distinguished from its parent and all other varieties of *Corylopsis spicata* of which I am aware in showing a distinctive yellow foliage color rather than the bluish-green color of the parent.

The accompanying photographic illustration shows a specimen of the new cultivar as true to color as is reasonably possible to make in an illustration of this character.

FIG. 1 illustrates the distinctive golden yellow foliage of the new variety.

DETAILED DESCRIPTION OF THE NEW VARIETY

'GOLDEN SPRING' has not been observed under all possible environmental, cultural, and light conditions. The following observations and descriptions are of 7-year-old plants grown in 5-gallon nursery containers in under conditions in July, in Forest Grove, Oreg., under 50% shade. In this description, color references are to The Royal Horticultural Society Colour Chart (1995) and terminology used in the color descriptions herein refers to plate numbers in this color chart. Phenotypic expression may vary with light intensity, cultural, and environmental conditions.

CLASSIFICATION

Botanical: *Corylopsis spicata* Sieb. & Zucc. 'GOLDEN SPRING'.

Parentage: Chance seedling (natural mutation) in a controlled planting of *Corylopsis spicata* (unnamed, unparented).

Propagation: By grafting and vegetative cuttings.

PLANT

Size: Mature plant can be 1.5 to 3 meters high with a spread of about 2 to 4 meters at maturity.

Habit: A wide, spreading shrub often twice as wide as high.

LEAF DESCRIPTION

Arrangement: Alternate.

Leaf shape: Simple, orbicular-ovate or orbicular-obovate.

*Apex.*—Acuminate to abruptly short acuminate.

*Base.*—Rounded to cordate to obliquely cordate.

Leaf size: 4 to 11 cm long, 4 to 9 cm wide.

Leaf margin: Sinuate-denticulate with bristle-like teeth.

Leaf texture and substance:
*Adaxial.*—Glabrous.
*Abaxial.*—Glaucous and pubescent.
Venation: Palmately veined with 6 to 7 vein pairs.
Immature leaf color: Near Yellow Group 4A and 5B; margins near Red-Purple Group 58A.
Mature leaf color: Near Yellow Group 4A and 5B.
Petioles: Petiole 1 to 2.5 cm long and densely pubescent.
Hardiness: USDA Zone 5 (−20° to −10° F.).
Vigor: Moderately vigorous; younger specimens grow to 50 cm per year.
Pests/diseases: No resistance or susceptibility to pests or disease problems beyond that of the species has been noted.
Color of mature leaves: (Color readings from conditions in July, Forest Grove, Oreg., under 50% shade) Near 4A, Near 5B.
*Hardiness.*—USDA Zone 5 (−20° to −10° F.).

INFLORESCENCE

Bloom period: March, before foliage emerges, through April.
Lastingness of individual bloom: 2 to 3 weeks.
Floral arrangement: Pendulous spike with 7 to 10 sessile flowers, each flower subtended by a single bract, borne on previous season's growth.
Bracts: Bracts are concave, 3-lobed; approximately 2 mm to 7 mm long, the longer bracts located at the base of the spike; the entire spike is subtended by several concave bracts approximately 12 mm to 15 mm long.
Flower size: 10 mm to 12 mm long; 8 mm to 10 mm wide.
Sepals:
*Average quantity of sepals.*—5.
*Shape.*—Obovate; acutely pointed.
*Aspect.*—Concave.
*Size.*—1 mm to 2 mm long; less than 1 mm across.
*Color.*—Near Yellow-Green Group 150C.
*Bracts.*—Pubescent, especially when young, glabrous on outside.
*Calyx.*—Nearly glabrous.
*Buds.*—Shape; Ovoid; acute apices. Size: 8 mm to 10 mm long.
Fragrance: None noted.

REPRODUCTIVE SYSTEM

Stamens: 5; about 10 mm to 12 mm long; near Yellow-Green Group 150C; abaxial portion is pale reddish green.
Pistils: 1; Near Yellow-Green Group 150C.
Anthers: Near Red-Purple Group 59A. Fruit: 2-beaked capsule, pubescent, 7 to 8 mm across.
Seed capsule color: Near Greyed Orange Group 166C. Seed color: Near Brown Group 200B.

I claim:

1. A new plant variety of *Corylopsis spicata* of the variety substantially as shown and described.

* * * * *